(12) United States Patent
Anderson et al.

(10) Patent No.: US 10,668,275 B2
(45) Date of Patent: Jun. 2, 2020

(54) ELECTRICAL LEADS FOR MEDICAL USE

(75) Inventors: Neil L. Anderson, Roseville (AU);
Norman Booth, Wattle Grove (AU);
Evan K. Chong, South Strathfield (AU)

(73) Assignee: CATHRX LTD, Everleigh, New South Wales (AU)

(*) Notice: Subject to any disclaimer, the term of this patent is extended or adjusted under 35 U.S.C. 154(b) by 1405 days.

(21) Appl. No.: 13/598,506

(22) Filed: Aug. 29, 2012

(65) Prior Publication Data

US 2012/0330121 A1 Dec. 27, 2012

Related U.S. Application Data

(63) Continuation of application No. 11/659,246, filed as application No. PCT/AU2005/000834 on Jun. 10, 2005, now Pat. No. 8,286,338.

(60) Provisional application No. 60/599,651, filed on Aug. 5, 2004, provisional application No. 60/648,232, filed on Jan. 28, 2005.

(51) Int. Cl.
*A61B 5/04* (2006.01)
*A61B 18/18* (2006.01)
*A61N 1/05* (2006.01)
*A61B 18/14* (2006.01)

(52) U.S. Cl.
CPC .......... *A61N 1/056* (2013.01); *A61B 18/1492* (2013.01); *Y10T 29/49117* (2015.01); *Y10T 29/49156* (2015.01); *Y10T 29/49162* (2015.01); *Y10T 29/49224* (2015.01)

(58) Field of Classification Search
CPC ................ A61N 1/056; A61B 18/1492; A61B 2017/00243; A61B 17/0057; A61B 2017/00247; A61B 2018/1467; A61B 2018/1437; A61B 17/3417; A61B 2017/3454

USPC ........ 600/372–393, 431, 433, 435, 508–509; 606/20–41; 607/122–125
See application file for complete search history.

(56) References Cited

U.S. PATENT DOCUMENTS 2,002,267 A 5/1935 Kyle
3,378,507 A 4/1968 Sargent et al.
(Continued)

FOREIGN PATENT DOCUMENTS

EP 0101595 2/1984
EP 0479435 4/1992
(Continued)

OTHER PUBLICATIONS

Supplementary Partial European Search Report for Application No. 05749667.1, dated Jun. 2, 2012, 4 pages.
(Continued)

*Primary Examiner* — Eun Hwa Kim
*Assistant Examiner* — Brian M Antiskay
(74) *Attorney, Agent, or Firm* — TraskBritt (57) ABSTRACT

A process for manufacturing an electrical lead having one or more electrodes includes providing an elongate member having at least one polymeric region and further having at least one electrical conductor that extends along at least a part of a length of the elongate member and that is contained in a wall of the elongate member. A length of the at least one electrical conductor is accessed at the at least one polymeric region. An electrically conductive adhesive is applied to the length of the at least one electrical conductor that has been accessed.

9 Claims, 9 Drawing Sheets

(56) References Cited

U.S. PATENT DOCUMENTS

| | | | |
|---|---|---|---|
| 3,460,540 A * | 8/1969 | Gagne | A61M 25/1027 604/103 |
| 3,769,984 A * | 11/1973 | Muench | A61N 1/056 607/122 |
| 4,101,984 A | 7/1978 | MacGregor | |
| 4,141,366 A | 2/1979 | Cross et al. | |
| 4,274,417 A * | 6/1981 | Delpy | A61M 25/0068 600/364 |
| 4,467,020 A | 8/1984 | Puglisi | |
| 4,592,808 A | 6/1986 | Doubt | |
| 4,672,970 A | 6/1987 | Uchida et al. | |
| 4,690,155 A * | 9/1987 | Hess | A61B 5/0422 607/122 |
| 4,734,296 A | 3/1988 | Schramm | |
| 4,776,334 A | 10/1988 | Prionas | |
| 4,833,568 A | 5/1989 | Berhold et al. | |
| 4,955,382 A * | 9/1990 | Franz | A61B 5/042 600/375 |
| 4,992,339 A | 2/1991 | Georgopoulos et al. | |
| 5,029,585 A * | 7/1991 | Lieber | A61B 5/0215 600/396 |
| 5,130,842 A | 7/1992 | Gauthier et al. | |
| 5,269,810 A | 12/1993 | Hull et al. | |
| 5,279,781 A | 1/1994 | Yamasaki | |
| 5,302,810 A | 4/1994 | Gauthier et al. | |
| 5,330,520 A | 7/1994 | Maddison et al. | |
| 5,443,742 A | 8/1995 | Mader et al. | |
| 5,489,277 A * | 2/1996 | Tolkoff | A61B 6/12 604/529 |
| 5,522,874 A | 6/1996 | Gates | |
| 5,554,176 A | 9/1996 | Maddison et al. | |
| 5,554,178 A | 9/1996 | Dahl et al. | |
| 5,609,622 A | 3/1997 | Soukup et al. | |
| 5,718,231 A | 2/1998 | Dewhurst et al. | |
| 5,782,900 A * | 7/1998 | de la Rama | A61B 18/1492 600/374 |
| 5,810,802 A * | 9/1998 | Panescu | A61B 5/0422 374/E1.005 |
| 5,834,051 A | 11/1998 | Woloszko et al. | |
| 5,840,031 A * | 11/1998 | Crowley | A61B 8/12 600/440 |
| 5,853,409 A * | 12/1998 | Swanson | A61B 18/00 606/31 |
| 5,931,862 A | 8/1999 | Carson | |
| 5,964,757 A * | 10/1999 | Ponzi | A61B 18/24 606/15 |
| 6,032,061 A | 2/2000 | Koblish et al. | |
| 6,071,278 A | 6/2000 | Panescu et al. | |
| 6,249,708 B1 * | 6/2001 | Nelson | A61N 1/056 607/122 |
| 6,357,447 B1 * | 3/2002 | Swanson | A61B 5/0422 128/898 |
| 6,371,955 B1 * | 4/2002 | Fuimaono | A61B 18/1492 606/29 |
| 6,440,488 B2 | 8/2002 | Griffin, III et al. | |
| 6,458,127 B1 | 10/2002 | Truckai et al. | |
| 6,534,581 B1 | 3/2003 | Kleyer et al. | |
| 7,178,234 B2 | 2/2007 | Kawasaki et al. | |
| 7,395,116 B2 * | 7/2008 | Mehdizadeh | A61N 1/056 600/373 |
| 7,625,617 B1 | 12/2009 | Anderson et al. | |
| 7,629,015 B2 | 12/2009 | Anderson et al. | |
| 7,879,387 B2 | 2/2011 | Myers | |
| 7,899,548 B2 | 3/2011 | Barker | |
| 2002/0198446 A1 | 12/2002 | Hill et al. | |
| 2003/0139794 A1 | 7/2003 | Jenney | |
| 2004/0068313 A1 | 4/2004 | Jenney et al. | |
| 2004/0111141 A1 * | 6/2004 | Brabec | A61N 1/0556 607/119 |
| 2005/0065508 A1 * | 3/2005 | Johnson | A61B 5/0422 606/41 |
| 2005/0131513 A1 | 6/2005 | Myers | |
| 2005/0227398 A1 | 10/2005 | Anderson et al. | |
| 2010/0036376 A1 | 2/2010 | Anderson et al. | |
| 2012/0035605 A1 * | 2/2012 | Tegg | A61B 34/73 606/41 |
| 2012/0310239 A1 * | 12/2012 | Stewart | A61B 18/1492 606/41 |

FOREIGN PATENT DOCUMENTS

| | | |
|---|---|---|
| EP | 0627234 | 12/1994 |
| EP | 0778046 | 6/1997 |
| EP | 0790625 | 8/1997 |
| GB | 2268071 | 1/1994 |
| JP | H03-506097 | 12/1991 |
| JP | H08-511185 | 11/1996 |
| WO | WO90/08466 | 8/1990 |
| WO | WO92/22687 | 12/1992 |
| WO | WO94/17852 | 8/1994 |
| WO | WO94/28804 | 12/1994 |
| WO | WO95/13844 | 5/1995 |
| WO | WO96/36860 | 11/1996 |
| WO | WO98/58681 | 12/1998 |
| WO | WO99/49932 | 10/1999 |
| WO | WO00/28894 | 5/2000 |
| WO | WO02/32497 | 4/2002 |
| WO | WO02/068042 | 9/2002 |
| WO | WO03/094722 | 11/2003 |
| WO | WO06/012671 | 2/2006 |

OTHER PUBLICATIONS

Amendment in Response to Final Office Action dated Jan. 22, 2009, for U.S. Appl. No. 10/399,845, filed Oct. 19, 2001, eighteen pages.
Supplementary Partial European Search Report for EP Application No. 05 74 9667, dated Jan. 31, 2012, 4 pages.
Amendment in Response to Final Office Action dated Aug. 15, 2008, for U.S. Appl. No. 11/123,392, filed May 5, 2005, six pages.
Amendment in Response to Non Final Office Action dated Jun. 17, 2009, for U.S. Appl. No. 10/399,845, filed Oct. 19, 2001, sixteen pages.
Amendment in Response to Non-Final Office Action dated May 5, 2009, for U.S. Appl. No. 11/123,392, filed May 5, 2005, four pages.
Amendment in Response to Non-Final Office Action dated Mar. 27, 2008, for U.S. Appl. No. 10/399,845, filed Oct. 19, 2001, twenty-one.
(Intl Date) Oct. 19, 2001, twelve pages.
Final Office Action dated Jul. 22, 2008, for U.S. Appl. No. 10/399,845, filed Oct. 19, 2001, twelve pages.
Final Office Action dated Apr. 7, 2008, for U.S. Appl. No. 11/123,392, filed May 5, 2005, eight pages.
Interview Summary dated Jun. 11, 2009, for U.S. Appl. No. 11/123,392, filed May 5, 2005, two pages.
Non-Final Office Action dated Apr. 2, 2009, for U.S. Appl. No. 10/399,845, filed Oct. 19, 2001, nine pages.
Non-Final Office Action dated Dec. 19, 2008, for U.S. Appl. No. 11/123,392, filed May 5, 2005, seven pages.
Non-Final Office Action dated Dec. 27, 2007, for U.S. Appl. No. 10/399,845, filed Oct. 19, 2001, ten pages.
Supplemental Response to Non-Final Office Action dated Jun. 17, 2009, for U.S. Appl. No. 11/123,392, filed May 5, 2005, eight pages.
European Search Report dated Mar. 31, 2008, for EP Application No. 07024785.3, filed Apr. 29, 2002, three pages.
Supplementary European Search Report dated Jun. 4, 2007, for EP Application No. 01977995.8, seven pages.
Requirement for Restriction dated Mar. 23, 2005, for U.S. Appl. No. 10/399,845, filed Oct. 19, 2001, four pages.
Response to Restriction Requirement dated Apr. 25, 2005, for U.S. Appl. No. 10/399,845, filed Oct. 19, 2001, two pages.
Non-Final Office Action dated Jul. 13, 2005, for U.S. Appl. No. 10/399,845, filed Oct. 19, 2001, nine pages.
Amendment in Response to Non-Final Office Action dated Oct. 12, 2005, for U.S. Appl. No. 10/399,845, filed Oct. 19, 2001, fourteen pages.
Interview Summary dated Oct. 18, 2005, for U.S. Appl. No. 10/399,845, filed Oct. 19, 2001, two pages.

(56) References Cited

OTHER PUBLICATIONS

Non-Final Office Action dated Dec. 30, 2005, for U.S. Appl. No. 10/399,845, filed Oct. 19, 2001, twelve pages.
Amendment in Response to Non-Final Office Action dated Mar. 29, 2006, for U.S. Appl. No. 10/399,845, filed Oct. 19, 2001, eighteen pages.
Interview Summary dated Apr. 27, 2006, for U.S. Appl. No. 10/399,845, filed Oct. 19, 2001, two pages.
Final Office Action dated Jun. 29, 2006, for U.S. Appl. No. 10/399,845, filed Oct. 19, 2001, thirteen pages.
Interview Summary dated Sep. 26, 2006, for U.S. Appl. No. 10/399,845, filed Oct. 19, 2001, one page.
Amendment After Final Action dated Oct. 5, 2006, for U.S. Appl. No. 10/399,845, filed Oct. 19, 2001, twenty-four pages.
Non-Final Office Action dated Oct. 26, 2006, for U.S. Appl. No. 10/399,845, filed Oct. 19, 2001, sixteen pages.
Interview Summary dated Dec. 27, 2006, for U.S. Appl. No. 10/399,845, filed Oct. 19, 2001, one page.
Amendment in Response to Non-Final Office Action dated Jan. 5, 2007, for U.S. Appl. No. 10/399,845, filed Oct. 19, 2001, twenty-five pages.
Final Office Action dated Apr. 5, 2007, for U.S. Appl. No. 10/399,845, filed Oct. 19, 2001, seven pages.
Amendment After Final Action dated Jun. 5, 2007, for U.S. Appl. No. 10/399,845, filed Oct. 19, 2001, twenty-one pages.
Advisory Action dated Jun. 15, 2007, for U.S. Appl. No. 10/399,845, filed Oct. 19, 2001, fourteen pages.
Non-Final Office Action dated Dec. 12, 2006, for U.S. Appl. No. 11/123,392, filed May 5, 2005, six pages.
Amendment and Response to Restriction Requirement dated Jan. 9, 2007, for U.S. Appl. No. 11/123,392, filed May 5, 2005, six pages.
Non-Final Office Action dated Mar. 26, 2007, for U.S. Appl. No. 11/123,392, filed May 5, 2005, six pages.
Amendment in Response to Non-Final Office Action dated Jun. 25, 2007, for U.S. Appl. No. 11/123,392, filed May 5, 2005, ten pages.
European Search Report dated Feb. 12, 2007, for EP Application No. 01977995.8 filed on Oct. 19, 2001, five pages
International Search Report and Written Opinion dated Jul. 11, 2005, for PCT Application No. PCT/AU2005/000834, filed Jun. 10, 2005, six pages.
International Preliminary Report on Patentability dated Feb. 6, 2007 for PCT Application No. PCT/AU2005/000834.
Japanese Search Report dated Dec. 7, 2010, for JP Application No. P2007-524128, 4 pages.
Australian Search Report dated May 26, 2010, for AU Application No. 2005269248, 2 pages.
Australian Search Report dated Apr. 20, 2011, for AU Application No. 2005269248, 2 pages.
Extended European Search Report for EP Application No. 14163461.8 dated Oct. 6, 2014, 8 pages.
European Office Action for European Application No. 14163461.8 dated Sep. 12, 2017, 8 pages.
Summons to Attend Oral Proceedings, EU Application No. 14163461.8, dated May 8, 2018, 8 pages.
Chinese First Office Action for Chinese Application No. 201010117983 dated Dec. 31, 2010, 8 pages with English Translation.
Japanese Notice of Reasons for Refusal for Japanese Application No. 2007-524128, dated Nov. 30, 2010, 6 pages with English Translation.
Japanese Written Opinion for Japanese Application No. 2007-524128, dated Mar. 2, 2011, 6 pages with English Translation.

\* cited by examiner

ELECTRICAL LEADS FOR MEDICAL USE

CROSS-REFERENCE TO RELATED APPLICATIONS

This application is a continuation of U.S. patent application Ser. No. 11/659,246, filed Feb. 25, 2008, now U.S. Pat. No. 8,286,338, issued Oct. 16, 2012, which is a national phase entry under 35 U.S.C. § 371 of International Application No. PCT/AU2005/000834 filed Jun. 10, 2005, which claims priority from U.S. Provisional Patent Application Nos. 60/599,651, filed Aug. 5, 2004, and 60/648,232, filed Jan. 28, 2005, the contents of each of which applications are incorporated herein by this reference in their entirety.

FIELD

This invention relates to the manufacture of an electrical lead and, more particularly, to a process for manufacturing an electrical lead, such as an electrically conductive catheter, and to an electrical lead.

BACKGROUND

The electrical activity of the muscles in the heart directs the overall activity of the heart. Many heart malfunctions, particularly arrhythmias, are evidenced by or caused by electrical activity that is not suitable for the heart's normal functioning. The electrical leads described herein are useful in the detection of the heart's electrical activities and in its treatment by stimulation, ablation and defibrillation.

Electrical leads having electrode regions have been used in the medical field for applications such as those referred to above.

Traditionally, the electrodes have been made from machined metal or coiled wire components that, while having the requisite electrical conductivity, fail to provide the desired degree of flexibility required in a medical application.

Although the use of metal coated or metal-filled polymers as medical electrodes has been considered, the amount of metal required to obtain a suitable level of conductivity renders the resultant lead stiff and not particularly suitable for implantation into a patient.

SUMMARY

According to a first aspect of the invention, there is provided a process for manufacturing an electrical lead having one or more electrodes, the process including:
  providing an elongate member having at least one polymeric region and further having at least one electrical conductor that extends along at least a part of a length of the elongate member and that is contained in a wall of the elongate member;
  accessing a length of the at least one electrical conductor at the at least one polymeric region; and
  applying an electrically conductive adhesive to the length of the at least one electrical conductor that has been accessed.

One or more discrete electrodes may be formed along a length of the elongate member. The electrodes may comprise bands that extend at least partially around the circumference of the elongate member.

The electrically conductive adhesive may comprise any of a variety of materials ranging from inherently conductive adhesives, adhesive bases containing solid conductive fillers, adhesive bases containing dissolved conductive materials, and mixtures of these materials. Adhesive bases comprising curable or settable polymeric materials, e.g., polymers that are not tacky or sticky after curing or setting, are also suitable for this purpose. Epoxies containing particulate or fibrillar metals are suitable choices, particularly highly conductive, biocompatible metals such as silver, gold, platinum, palladium, rhodium, and their mixtures as well as alloys containing those metals and constructs of those metals having regions of differing composition. One choice may comprise a silver-filled epoxy.

A further step of applying at least one electrically conductive material to the electrically conductive adhesive may be carried out. Again, the electrically conductive material may be any of a variety of materials, but particularly suitable are those that are able to form a conductive layer between the conductive adhesive and any additional material placed externally to the at least one electrically conductive material.

One appropriate class of such electrically conductive materials, those that are to be applied to the adhesive, may be a class of liquid carriers, particularly volatile carriers such as solvents, variously containing solvated or complexed conductors or containing solid conductors. A subclass of these materials may be inks containing particulate conductive metals, alloys or constructs such as silver or silver coated with a metal such as platinum or palladium.

The electrically conductive adhesive or the electrically conductive material applied to the electrically conductive adhesive may be further overlaid with a conductive metal such as those described above. The metal may comprise platinum.

The elongate member may include a plurality of electrical conductors and the process may include accessing a length of each of a plurality of the electrical conductors at circumferentially spaced intervals about the elongate member and applying a pad of the electrically conductive adhesive to the accessed length of each electrical conductor.

The process may include applying a layer of at least one electrically conductive material to each pad of electrically conductive adhesive. Further, the process may include overlaying each pad of electrically conductive adhesive with a metal layer including platinum or palladium.

The pads of electrically conductive adhesive may be arranged in a longitudinally aligned relationship about the circumference of the elongate member and the process may include applying the metal layer about the circumference of the elongate member as a continuous layer and, thereafter, separating the layer into a plurality of electrically isolated segments, for example, by laser cutting, arranged at circumferentially spaced intervals to form a plurality of discrete electrodes arranged about the circumference of the elongate member.

The process may include applying the metal, including platinum, by mounting a ring over the elongate member and securing the ring in position. The ring may be secured by adhesive, crimping, or the like.

The electrical lead may include a number of conductors that extend along at least a part of a length of the electrical lead. Although one or more conductors may be specifically associated with an electrode, the electrical lead may include further conductors that form part of a temperature-sensing member. A temperature-sensing member may be associated with an electrode in such a way that it determines the temperature at the electrode. To determine the temperature at the electrode, the temperature-sensing member may be electrically isolated from a corresponding electrode.

The process may, therefore, include the further step of isolating an electrical contact of the electrical lead from the one or more electrodes. The electrical contact may be isolated by accessing the electrical contact, applying an electrically conductive adhesive to the first electrical contact, and electrochemically treating the electrically conductive adhesive such that a portion of the electrically conductive adhesive is converted to an electrically non-conductive portion.

The electrochemical treatment may include a step of passing a current through the electrical contact such that a current also passes through the electrically conductive adhesive while the electrically conductive adhesive is in an ionic environment containing a material tending to form an insulator (or high resistance layer) with some component of the electrical contact. An ionic environment comprising a saline (NaCl) solution or potassium chloride solution may be suitable, although other such materials are envisaged.

Such a step converts a metal in the electrically conductive adhesive electrochemically to a metal chloride. Where the electrically conductive adhesive comprises a silver-filled epoxy, the silver situated on surfaces facing the solution surface is converted to silver chloride. That silver chloride layer may act as an insulating layer.

The electrical contact may comprise a part of a temperature-sensing member, such as a thermocouple.

According to a second aspect of the invention, there is provided a process of electrically isolating a first electrical contact of an electrical lead from a second electrical contact of the electrical lead, the process including accessing the first electrical contact, applying an electrically conductive adhesive to the first electrical contact, and electrochemically treating the electrically conductive adhesive such that a portion of the electrically conductive adhesive is converted to an electrically non-conductive portion.

The electrochemical treatment may comprise the step of passing a current through the electrical contact and, hence, through the electrically conductive adhesive to form an insulator. Similarly, to the step above, the step may be practiced in an ionic environment containing a reactive material to produce an insulator or highly resistive material. In the instance where silver-containing materials are chosen, a saline (NaCl) solution or potassium chloride solution may be suitable.

The electrically conductive adhesive may comprise those listed above, including silver-filled adhesives such as a silver-filled epoxy. Again, if so chosen, the silver in the portion of the adhesive may be converted to silver chloride (AgCl) using the electrochemical reaction step discussed above. The silver chloride formed is electrically non-conductive.

The first electrical contact may comprise a temperature-sensing member.

The second electrical contact may comprise an energy-transmitting electrode. The energy-transmitting electrode may transmit energy that creates heat in the tissue against which the electrode is placed in use.

The temperature-sensing member may be in thermal contact with the energy-transmitting electrode.

The temperature-sensing member in this variation and others described herein may comprise a thermocouple or other temperature-sensing devices, such as resistance temperature detectors (RTDs), thermistors, or integrate circuit (IC) temperature-sensing devices, in which the output of frequency or period is related to the temperature. If a thermocouple is chosen, an appropriate choice of conductors may comprise a first wire made of copper and a second wire made of Constantan.

The electrical lead may comprise an elongate member wherein the wires of the thermocouple extend along at least a part of a length of the elongate member and may be contained in a wall of the elongate member. A junction may be formed between the two wires of the thermocouple in proximity to the electrode to form a closed loop thermocouple by the application of the electrically conductive adhesive to the wires to bring the wires into electrical connection with each other at the junction.

At least one electrically conductive material may be applied over the electrode and the thermocouple junction.

Broadly, according to a third aspect of the invention, there is provided a process of manufacturing an electrical lead, the process including:

providing an elongate member having a proximal end and a distal end, at least one electrical conductor contained in the elongate member and extending from the proximal end toward the distal end of the elongate member, the at least one electrical conductor terminating in electrical connection with an electrically conductive zone arranged externally of the elongate member;

cutting the elongate member distally of the electrically conductive zone;

forming a non-conductive termination distally of the electrically conductive zone; and applying a conductive material over the electrically conductive zone and the termination to form an end electrode of the electrical lead.

More specifically, according to the third aspect of the invention, there is provided a process of manufacturing an electrical lead, the process including:

providing an elongate member having a proximal end and a distal end, the elongate member having one or more polymeric regions and further having a plurality of electrical conductors that extend along at least a part of a length of the elongate member toward the distal end of the elongate member, the electrical conductors being contained within a wall of the elongate member;

in respect of each of at least some of the electrical conductors, forming an electrically conductive zone in electrical contact with its associated electrical conductor by:

accessing a length of each of the at least some electrical conductors through the polymeric region of the elongate member and applying an electrically conductive adhesive to each accessed electrical conductor;

applying conductive material at an access point associated with each electrical conductor to form a plurality of longitudinally spaced electrically conductive zones along the length of the elongate member;

cutting the elongate member distally of one of the electrically conductive zones;

applying an electrically non-conductive termination distally of the one electrically conductive zone; and applying an electrically conductive material to bridge the electrically conductive zone and the termination to form an end electrode of the elongate member.

The termination may be applied in a liquid state. The termination may be applied in two stages.

Thus, a first layer may be applied to seal the distal end of the elongate member. A second layer may be applied and shaped to provide a desired shape to the end electrode.

The termination may be made from a suitable non-conductive material including a resin. The termination may, particularly, be a synthetic resin such as an epoxy resin.

Instead, the termination may be a solid element that is adhesively secured to the distal end of the elongate member both to seal the end and to form the desired shape of the end electrode.

The desired shape may be a substantially dome shape.

The electrically conductive material may be any of a variety of materials. Preferably, the electrically conductive material is applied in two stages. First, a first layer of an electrically conductive material may be applied in a liquid form. The liquid form may be a liquid carrier, particularly, volatile carriers such as solvents, and the liquid carrier may contain solvated or complexed conductive elements or may contain solid conductive elements. A subclass of these materials may be inks containing particulate conductive metals, alloys, or constructs such as silver.

As indicated above, the first layer may be applied to the electrically non-conductive termination and to the electrically conductive zone bridging the electrically conductive zone and the termination. This electrically conductive layer may be applied by any suitable means including brushing, dipping, pad printing, or the like.

The layer may be further overlaid with a conductive biocompatible material such as a suitable metal, for example, platinum.

According to a fourth aspect of the invention, there is provided an electrical lead that includes an elongate member having a proximal end and a distal end, at least one electrical conductor contained in the elongate member and extending from the proximal end toward the distal end of the elongate member, the at least one electrical conductor terminating in an electrically conductive zone arranged externally of the elongate member, a non-conductive termination arranged distally of the electrically conductive zone and at a distal end of the elongate member, and at least one layer of an electrically conductive material bridging the electrically conductive zone and the non-conductive termination to form an end electrode of an electrically conductive material.

According to a fifth aspect of the invention, there is provided a process of manufacturing an electrical lead, the process including providing an elongate member having a proximal end and a distal end, at least one electrical conductor contained in the elongate member and extending from the proximal end toward the distal end of the elongate member, the at least one electrical conductor terminating in electrical connection with an electrically conductive zone arranged externally of the elongate member, forming an access point in the elongate member to provide access to the at least one electrical conductor, applying a radiopaque material to a region of the elongate member longitudinally in register with the access point but out of electrical contact with the access point, and forming the electrically conductive zone by applying at least one layer of an electrically conductive material about the elongate member to be in electrical contact with the conductor through the access point and to overlie the radiopaque material.

According a sixth aspect of the invention, there is provided an electrical lead that includes an elongate member having a proximal end and a distal end, at least one electrical conductor contained in the elongate member and extending from the proximal end toward the distal end of the elongate member, an access point formed at a predetermined location in a wall of the elongate member to provide access to the electrical conductor, a zone of radiopaque material carried by the elongate member in a region of the elongate member longitudinally in alignment with the access point but circumferentially spaced from the access point, and at least one layer of an electrically conductive material carried at the predetermined location of the elongate member to provide electrical contact with the electrical conductor through the access point and to overlie the radiopaque material.

The access point may be in the form of a slit arranged transversely in a wall of the elongate member. In this regard, the elongate member may be in the form of a tubular member with a plurality of electrical conductors helically wound, and embedded in, the wall of the elongate member. Therefore, the slit may follow the direction of winding of the electrical conductors.

In one embodiment of this aspect of the invention, the radiopaque material may be a layer of radiopaque material applied to an external surface of the elongate member to form a cuff about the elongate member. The cuff may be in a diametrically opposed position to the access point on the elongate member. The radiopaque material may be applied by pad printing.

Thereafter, the process may include applying the layer of electrically conductive material. The layer of electrically conductive material may comprise a first layer, such as the silver ink referred to above. Thereafter, the first layer may be overlaid with a second, biocompatible electrically conductive material, such as platinum.

In another embodiment of this aspect of the invention, the radiopaque material may be inserted into a recess formed in the elongate member. The recess may be formed in a region of the elongate member diametrically opposed to the access point. The recess may be of any suitable shape such as, for example, a slot, a cruciform shape, a circle, or the like. In this embodiment, the conductive layer, may, once again, be applied in two stages. These layers may be applied by pad printing.

The radiopaque material may comprise approximately 70% to 80% non-conductive material and about 20% to 30% of adhesive material.

The adhesive material may comprise an epoxy. Preferably, the epoxy of the radiopaque material is matched to that of the silver ink to facilitate pad printing.

In the case where the radiopaque material is contained within a recess in the elongate member, the epoxy of the radiopaque material may be selected to be the same as that used in filling the access point. This is advantageous for biocompatibility purposes.

DETAILED DESCRIPTION

Figure 2A:
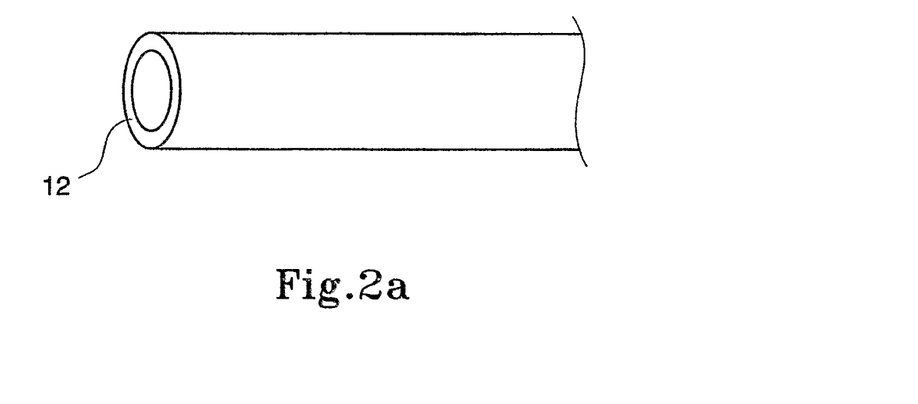
FIGS. 2a through 2f show, schematically, steps of a process, in accordance with an embodiment of the invention, for manufacturing the electrical lead of FIG. 1.
Figure 2B:
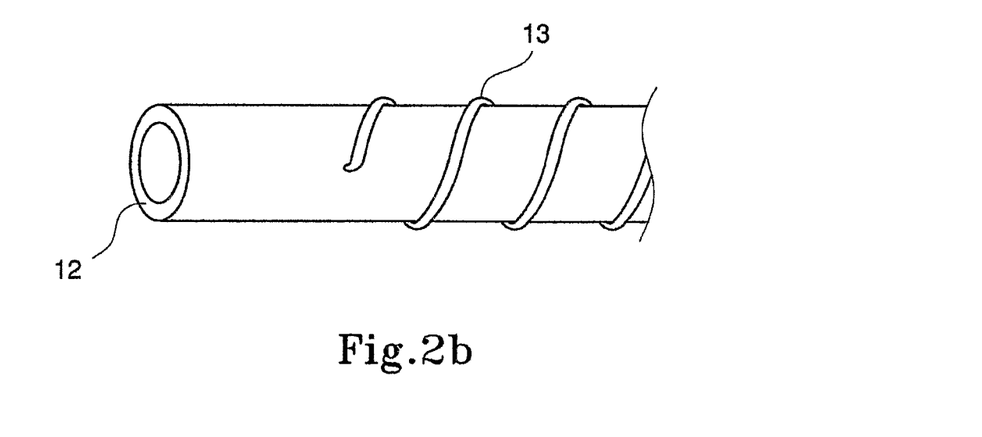
Figure 2C:
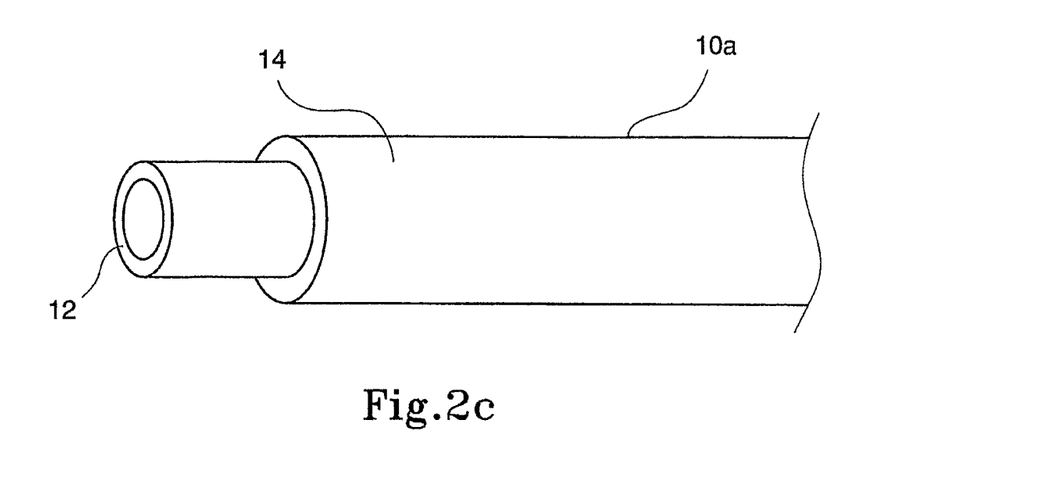
Figure 2D:
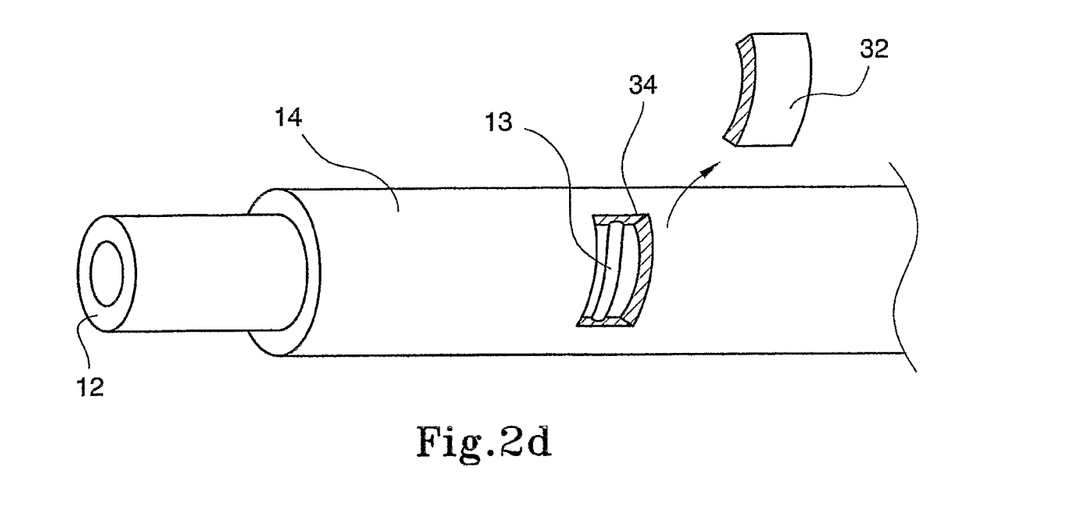
Figure 2E:
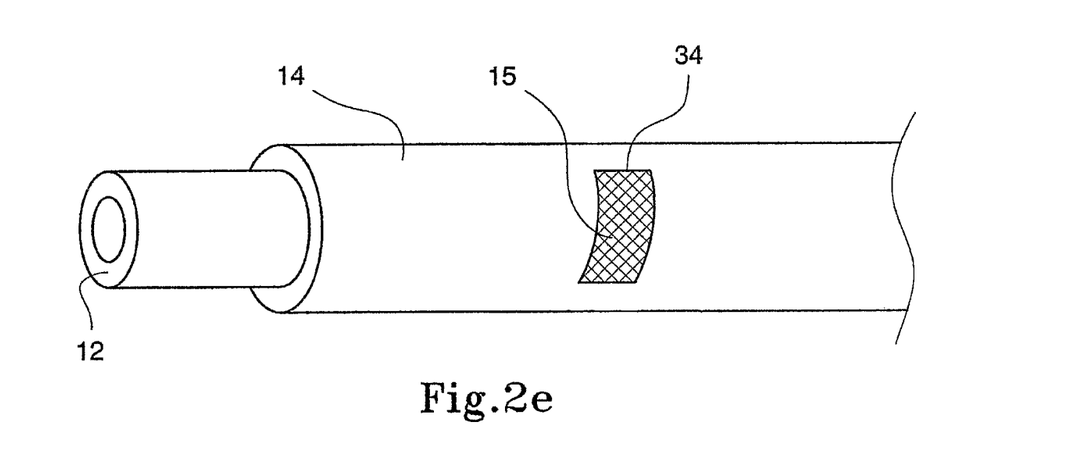
Figure 2F:
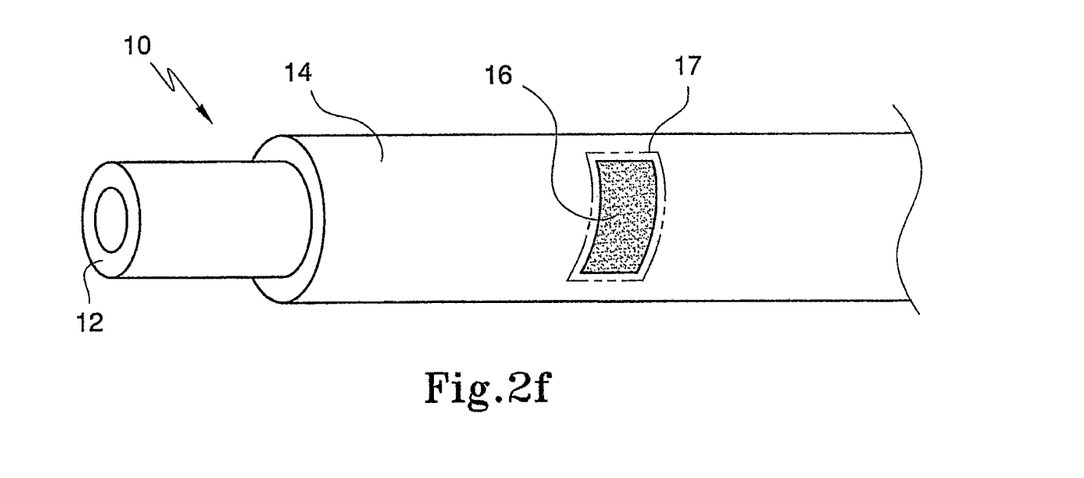

Referring to the drawings, an electrical lead made in accordance with a process for manufacturing an electrical lead, in accordance with an embodiment of the invention is generally designated by the reference numeral 10 (see FIG. 2f).

The electrical lead 10 comprises an elongate member 10a carrying at least one electrode 11 and, preferably, a number of band electrodes 11 positioned at longitudinally spaced intervals along the length of the elongate member 10a. An electrode not in the shape of a band is shown as 11b.

Figure 3:
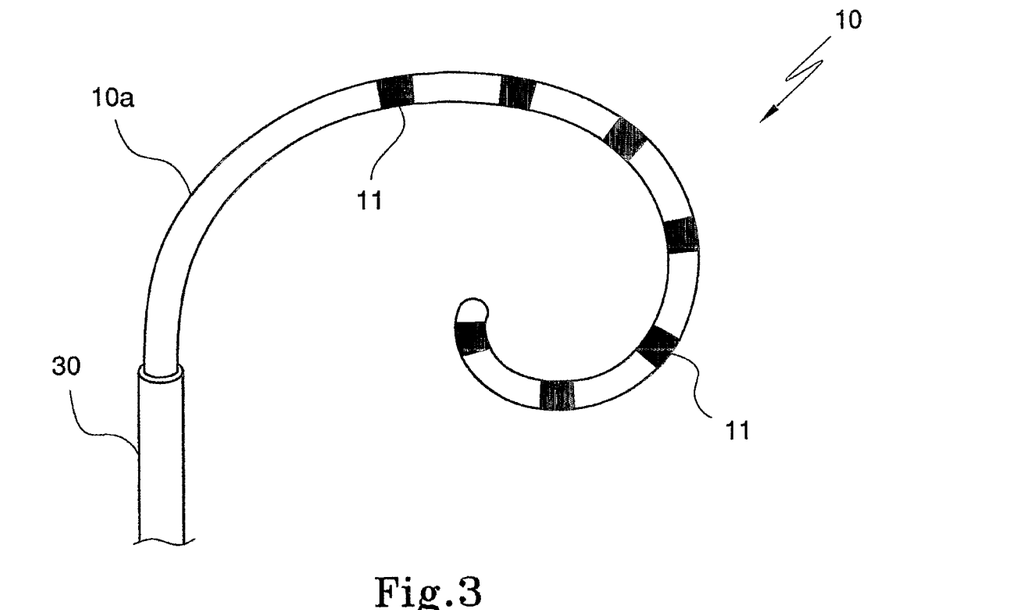
FIG. 3 is a schematic view of the electrical lead after completion of the process.

FIG. 3 shows a side view of the resulting electrical lead 10 functioning as an electrode sheath of a catheter and extending from an introducer 30 or a similar device. The lead 10 includes a plurality of longitudinally spaced electrodes 11, at least some of the electrodes 11 being band electrodes.

As described in the preceding paragraph, the electrical lead 10 is used as the electrode sheath of a cardiac catheter. The electrodes 11 are used as "sensing electrodes" to sense electrical activity (whether normal or not) in the muscles of the heart. In addition, the electrodes 11 may be used to ablate an area of tissue in the heart to correct some anomaly.

Thus, each electrode 11 may initially be operable as a sensing electrode. Such an electrode 11 enables a clinician to identify an area of electrical disturbance in the heart of a patient. The electrical disturbance may be caused by a damaged area of heart tissue that is "misfiring." Once located, the same electrode 11 may be switched to an ablation function to ablate the damaged tissue.

Multi-function electrodes 11 may be particularly useful in the treatment of atrial fibrillation. Atrial fibrillation, a cardiac arrhythmia, results when an area of cardiac tissue near the atrium "misfires." Such misfiring causes an electrical disturbance in the normal electrical pathway and in the resultant pulsatile contraction of the atrium. The result is that the atrium contracts in a fast and disorganized manner. If the fibrillation is prolonged, the blood in the atrium is not fully emptied into the ventricle, leading to a number of complications. By sensing the area of tissue that is causing the electrical disturbance, the precise area may then be ablated.

Production of the electrical lead 10 is shown in FIGS. 2a through 2f. Initially, as shown in FIG. 2a, an inner member 12 made from a suitable polymer such as polyethylene or polyether block amide (PEBAX) is provided. Other polymeric materials are also acceptable and easily identified from the art.

As shown in FIG. 2b, a plurality of conductors 13 is coiled in a helical manner around an outer surface of the inner member 12. Alternatively, the conductors 13 are housed within a lumen of the inner member 12. Up to twenty-four (24), or more, conductors 13 may be used in the electrical lead 10 (FIG. 2F) and are either helically wound around or are situated within the lumen of the inner member 12.

The conductors 13 are metal wires. The metal wires are insulated with a polymeric material such as nylon, polyurethane or a nylon-polyurethane co-polymer. Examples of suitable conductors include copper or Constantan coated with a nylon-polyurethane blend.

As shown in FIG. 2c, an outer polymeric jacket 14 is formed, for example, by extrusion, over the inner member 12 and the conductors 13 to form the elongate member 10a. The outer polymeric jacket 14 is made from materials similar to or the same as the materials of the inner member 12. Other materials may be selected as a matter of design choice, however.

The elongate member 10a comprising the inner member 12, the conductors 13 and the outer polymeric jacket 14 is heat-treated to secure the outer polymeric jacket 14 to the inner member 12 and to the conductors 13. It will be appreciated that a wall of the electrical lead 10 is therefore effectively made up of an inner layer defined by the inner member 12, a central layer made up of the helically wound conductors 13 and an outer layer defined by the outer polymeric jacket 14. The conductors 13 are, in effect, embedded in the wall and, as there is little, if any, polymeric material between adjacent turns of the conductors 13, there is the ability for limited movement between adjacent turns, thereby improving the flexibility of the electrical lead 10.

As shown in FIG. 2d, a desired length of one or more conductors 13 is accessed or exposed by laser (not shown) cutting a portion of the outer polymeric jacket 14. Laser cutting is accurate and provides a suitable way of removing a portion 32 of the outer polymeric jacket 14 with ease to produce an opening 34. The area of the opening 34 of the outer polymeric jacket 14 that has been removed is of a width similar to the width of the exposed conductors 13 and of a selected length extending along a predetermined length of the conductors 13, following the coiled or helical path of the conductors 13. The amount of outer polymeric jacket 14 that is removed largely depends upon the requirements of the final electrode 11. For example, there may be instances where it is desired to expose two or more adjacent conductors 13 to provide an electrode 11 with increased electrical conductivity and increased mechanical strength.

If the conductors 13 are insulated, the step of exposing the conductor(s) 13 also comprises cutting and removing the layer of insulation over the wires in addition to cutting and removing a corresponding portion of the outer polymeric jacket 14.

As shown in FIG. 2e, the opening 34 formed in the outer polymeric jacket 14 is substantially filled with an electrically conductive adhesive 15 of the types discussed above, such as a silver-filled epoxy. The conductors 13 coated with the electrically conductive adhesive 15 provide sufficient electrical conductivity to act as an electrode 11. Such an electrode 11 has particular application as a sensing electrode.

However, as shown in FIG. 2f, the process, preferably, further comprises a step of covering the electrically conductive adhesive 15 with a solvent that contains one or more conductive materials. The class of suitable materials is discussed above. These materials may be applied in a variety of ways, e.g., spraying, electrostatic deposition, direct application as by brush or pad, or the like. Good results are obtained using pad printing with a silver-filled ink or a palladium-filled ink or a palladium/silver ink 16.

Electrodes 11 formed in this manner, by pad printing an electrically conductive adhesive 15 with an electrically conductive ink 16, have a particular application as sensing electrodes. The process also includes a further step of catalyzing the pad printed ink 16 with an acidic palladium chloride solution to deposit a coating of palladium on the silver of the electrode 11.

The electrically conductive adhesive 15 or the pad printed coating of ink 16 is overlaid with a layer of platinum 17 to increase the electrical conductivity across the electrode. An electrode 11 that includes a layer of platinum 17 is suitable for ablation in addition to sensing. The layer of platinum 17 is applied to the electrode 11 by electroless plating but could also be applied by electrode deposition techniques.

The final electrode 11 may also be coated with a layer of material appropriate for prevention of metallic ions from the electrodes. An epoxy layer may be applied by pad printing. The epoxy prevents the migration of silver ions from the electrode 11.

Figure 4:
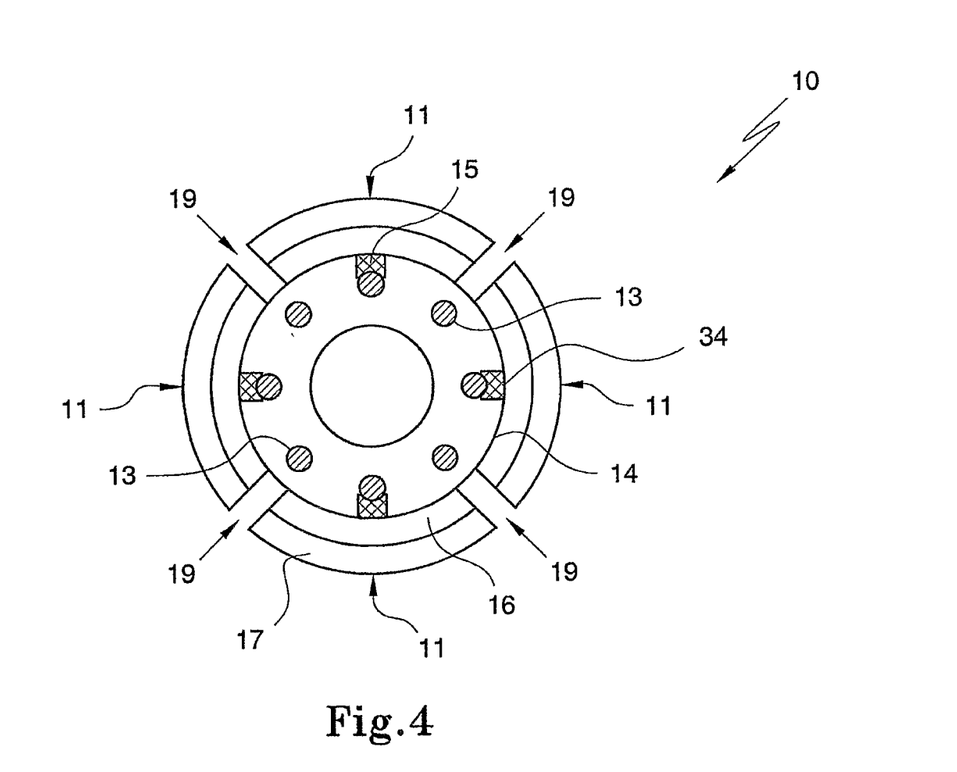
FIG. 4 is a schematic sectional end view of an electrical lead manufactured in accordance with a process of another embodiment of the invention.

In FIG. 4 of the drawings where, with reference to previous drawings, like reference numerals refer to like parts unless otherwise specified, another embodiment of the invention is illustrated. In this embodiment, a plurality of the electrical conductors 13 are accessed through excising a plurality of the portions 32 (not shown in FIG. 4 but shown in FIG. 2d) at circumferentially spaced intervals about the outer polymeric jacket 14 to form a plurality of circumferentially spaced openings 34. While FIG. 4 illustrates the openings 34 being in longitudinal alignment, it will be appreciated that the openings 34 could be staggered with respect to one another along the length of the outer polymeric jacket 14.

Each opening 34 is charged with the electrically conductive adhesive 15 and the layer 16 of electrically conductive material is pad printed about the circumference of the outer polymeric jacket 14 overlying the electrically conductive adhesive 15 in each of the openings 34. The biocompatible metal layer 17 is applied over the layer 16 of electrically conductive material.

Once the metal layer 17 has been applied, laser cuts 19 are made through the layers 16 and 17 to form a plurality of circumferentially spaced discrete electrodes 11. It will be appreciated that it is an advantage of this embodiment of the invention, that three-dimensional sensing or ablating can be effected. Also, it is easier to place a catheter with the electrical lead 10, as the orientation of the electrodes 11 of the electrical lead 10 relative to a site of a patient's body to be treated is less critical, as there is always likely to be at least one electrode 11 in contact with tissue.

Figure 5:
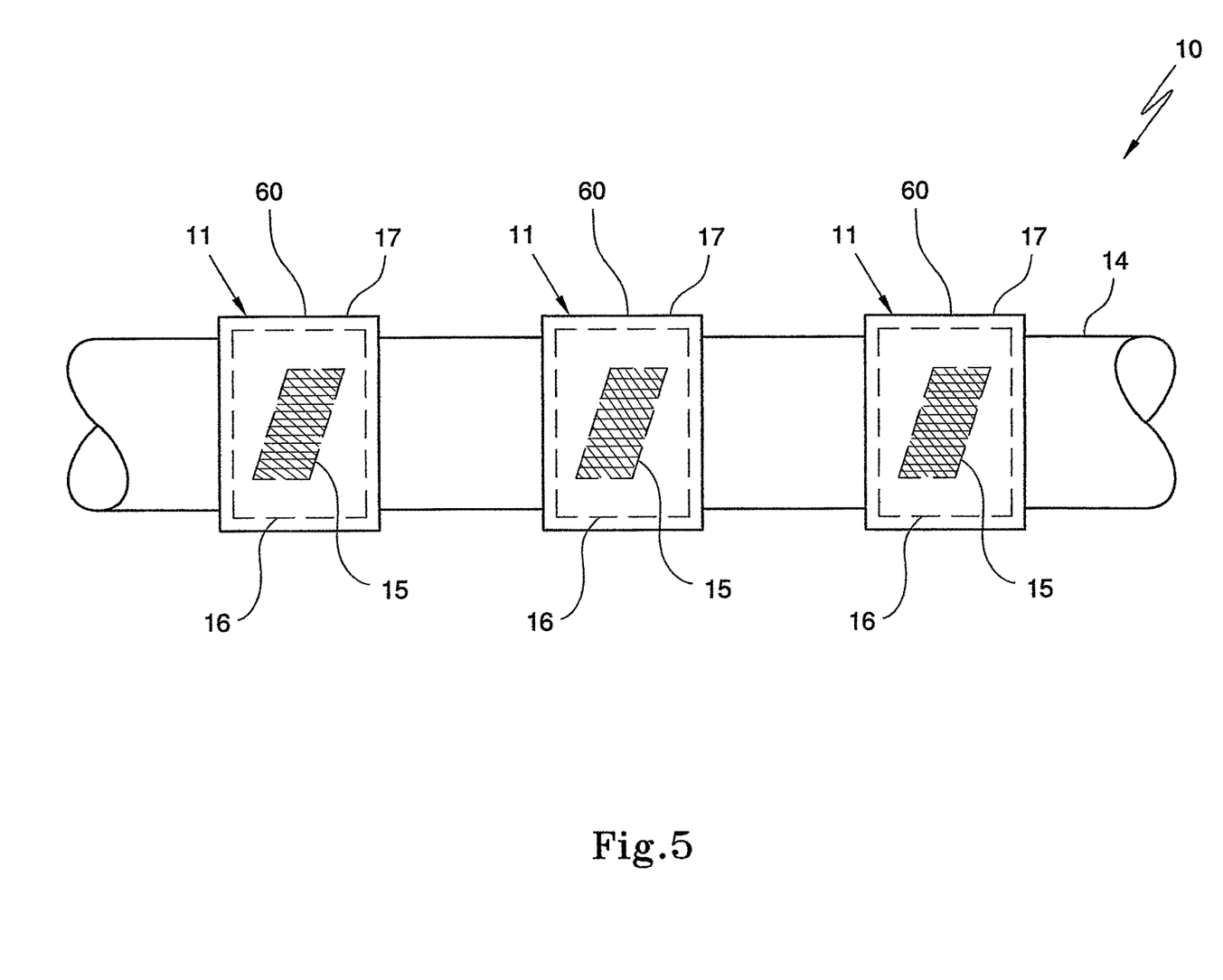
FIG. 5 is a schematic side view of a part of an electrical lead manufactured in accordance with a process of yet another embodiment of the invention.

Referring now to FIG. 5 of the drawings, yet a further embodiment of the invention is described. Once again, with reference to the previous drawings, like reference numerals refer to like parts unless otherwise specified.

In this embodiment, instead of the layer 17 of each electrode 11 being pad printed, a ring 60 is applied over the layer 16. The ring 60 is secured in position on the outer polymeric jacket 14 over its associated layer 16 by an appropriate securing technique, for example, an adhesive, crimping, being a press fit, or the like.

It is also useful to measure the temperature at an electrode 11, particularly in cases where the electrode 11 is used for ablation purposes. The electrical lead 10, therefore, includes a thermocouple 20 (FIG. 6b) or other suitable temperature measuring component.

Figure 6A:
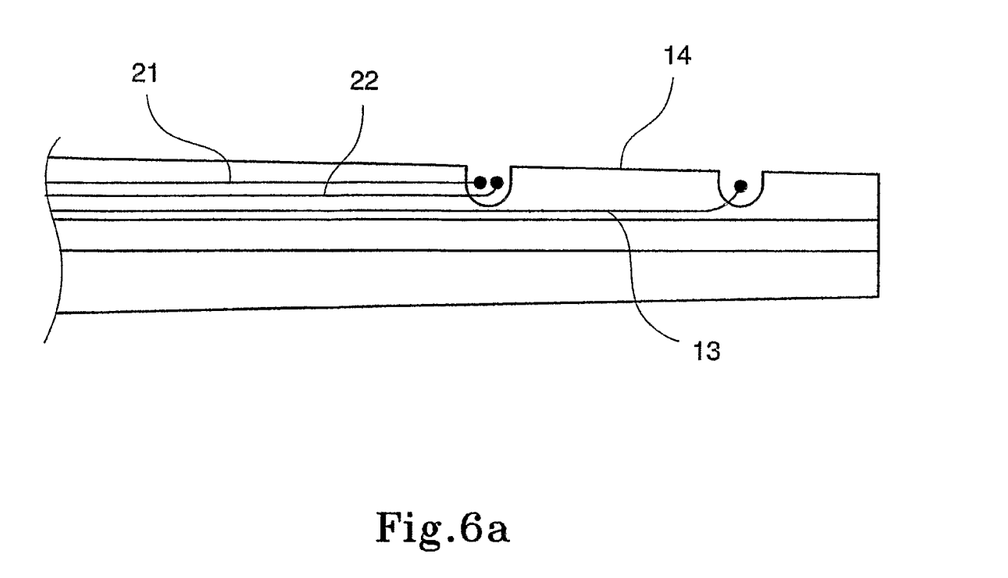
FIGS. 6a through 6d show, schematically, steps of a process, in accordance with a further embodiment of the invention, of electrically isolating a first electrical contact of an electrical lead from a second electrical contact of the electrical lead.
Figure 6B:
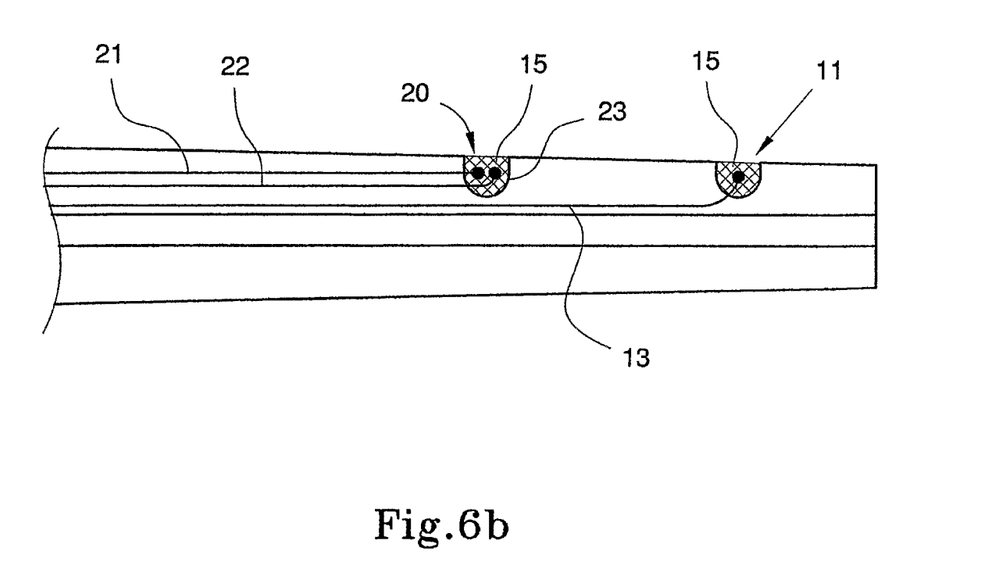

As shown in FIG. 6a, in a variation including the thermocouple 20, the thermocouple 20 comprises a first wire 21 made from copper and a second wire 22 made from Constantan. The outer polymeric jacket 14 is cut, for example, by laser cutting to expose the wires 21 and 22. An electrically conductive adhesive 15 is applied to the exposed wires 21, 22 as shown in FIG. 6b. The electrically conductive adhesive 15 brings the two wires 21 and 22 of the thermocouple 20 into electrical contact with each other thus providing a thermocouple junction 23.

Figure 6C:
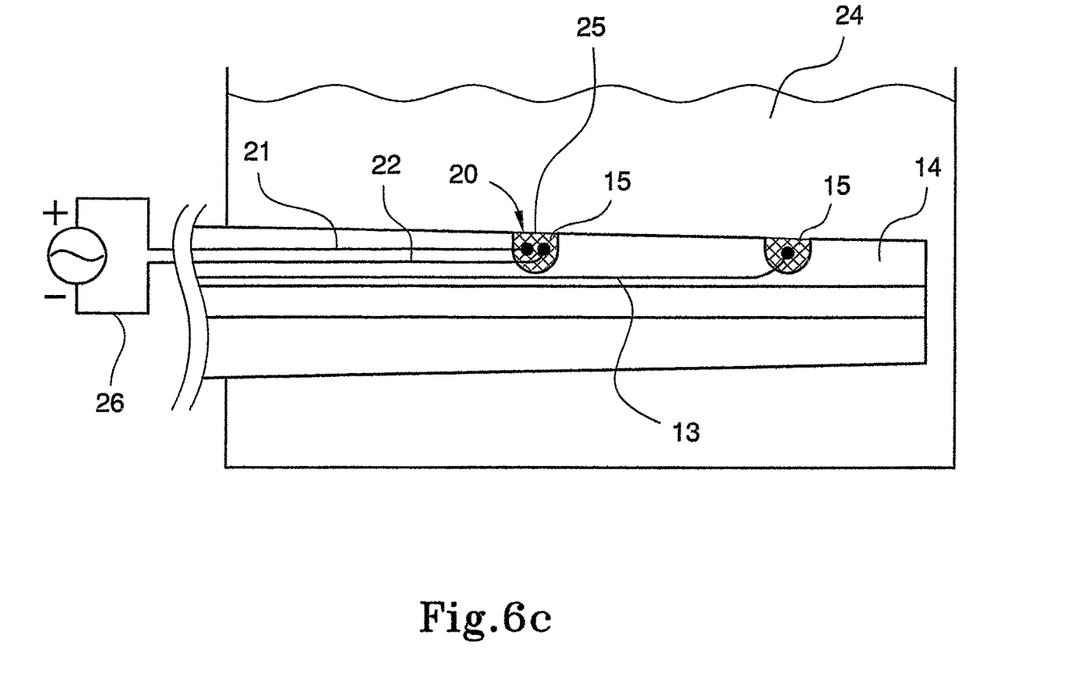

When forming the thermocouple 20 in this way and to ensure accurate temperature readings, the thermocouple 20 needs to be isolated from an associated electrode 11 as described in the steps below. As shown in FIG. 6c, after the wires 21 and 22 of the thermocouple 20 are exposed and the electrically conductive adhesive 15 has been applied to the exposed wires 21 and 22, the wires 21, 22 and electrically conductive adhesive 15 are exposed to a saline (NaCl) solution 24 and a current is passed through the wires 21 and 22 of the thermocouple 20 from a constant voltage source 26. The resultant current passing through the adhesive 15 causes a metal in the adhesive to convert to a metal chloride. When the adhesive 15 is a silver-filled epoxy, the silver on an outer facing surface of the electrically conductive adhesive 15 is converted to a relatively thin layer 25 of silver chloride and acts as a layer of insulation, electrically isolating the thermocouple 20 from the electrode 11 of the electrical lead 10.

Figure 6D:
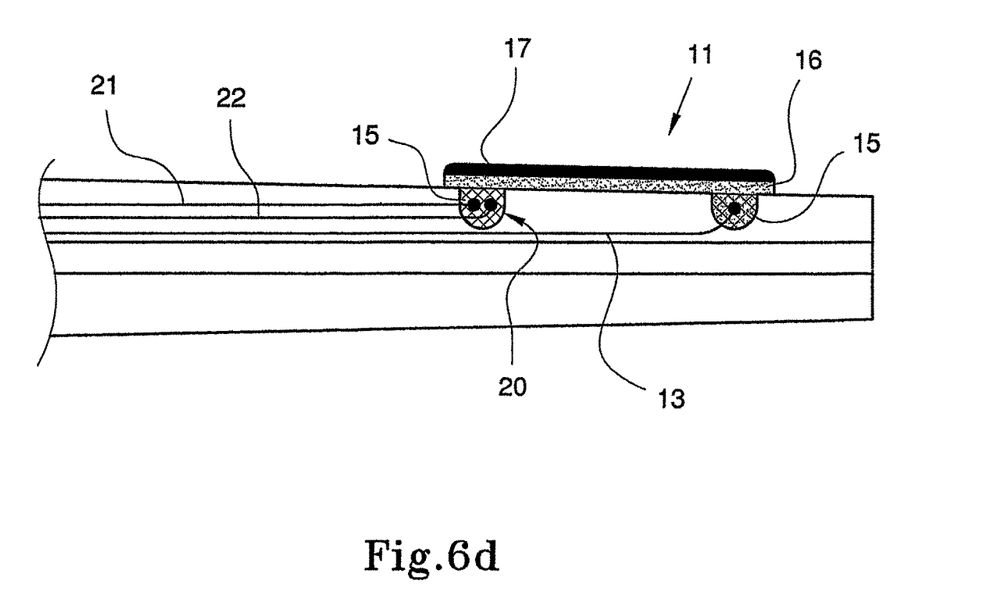

As shown in FIG. 6d, the adhesive 15 of the electrode 11 and the adhesive 15 of thermocouple 20 are then pad printed with a silver-filled ink 16 and a layer of platinum 17 is, optionally, applied to the ink 16.

The electrical lead 10 may comprise a single thermocouple 20 or, alternatively, a number of thermocouples. In the latter case, each electrode 11 formed on the electrical lead 10 may have a corresponding thermocouple 20.

EXAMPLE

A cable was sourced from Microhelix, Portland, Oreg. The cable had been prepared by extruding a PEBAX jacket over a polymer-coated wire mandrel. A mixture of nylon/polyurethane insulated copper and Constantan wires (each 0.125 mm) were helically coiled around the polymer-coated wire mandrel at a controlled pitch/coiling angle. The PEBAX jacket was then laid over the coiled wires. The resultant cable was cut to length and the mandrel removed. The cable was then heat-treated to secure the outer PEBAX jacket to the coiled wires.

Excimer laser cut windows were then cut over the individual wires at predetermined locations. The exact locations of the windows were programmed into the laser. The outer PEBAX jacket over the individual wire, together with the insulation layer of the wire, was removed without disturbing the wire beneath.

The openings formed by removal of the regions of PEBAX and insulation were filled with a silver-filled epoxy from Creative Materials Inc., Tyngsboro, Mass., using an air actuated dispenser. The silver-filled epoxy was cured at a temperature of about 140° C. and subsequently plasma treated in an argon atmosphere for approximately 1 min.

The silver-filled epoxy regions were then pad printed with a silver-filled ink. A plate with indentations relating to the size and spacing of the desired electrodes was wiped with the silver-filled ink, leaving ink behind in the indentations. A pad was then brought down over the top of the plate along the length of the ink-filled wells. The pad picked up the ink and was placed on the cable such that the inkpads corresponded with the regions of epoxy on the cable to deposit the ink on the cable over the regions of epoxy. This step was repeated a number of times as the cable was rotated such that a series of bands was formed around the circumference of the cable.

The cable was then cured in an oven at about 140° C. for up to 15 hours.

The bands of the cable were then further catalyzed with an acidic PdCl solution.

Finally, the cable was placed in a commercially available electroless Pt solution using hydrazine as the reducer for approximately 1 hour at about 60° C. A layer of platinum approximately 0.5 micron in thickness was formed over the bands to form final band electrodes.

Referring to FIGS. 7a through 7e of the drawings, a further embodiment of a process for manufacturing an electrical lead 10 is described. With reference to the previous drawings, like reference numerals refer to like parts unless otherwise specified.

In this embodiment of the invention, the electrodes 11 are formed at spaced intervals along a length of the elongate member 10a to be in electrical communication with the underlying conductors 13 (not shown in FIGS. 7a through 7e).

Figure 7A:
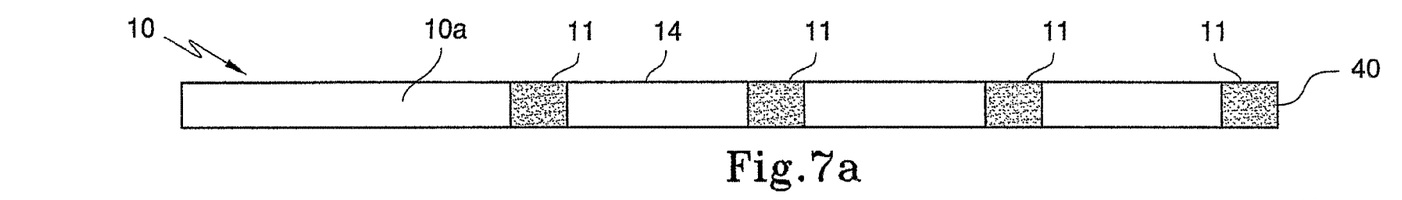
FIGS. 7a through 7e show, schematically, steps of a process, in accordance with yet a further embodiment of the invention, for manufacturing an electrical lead.
Figure 7B:
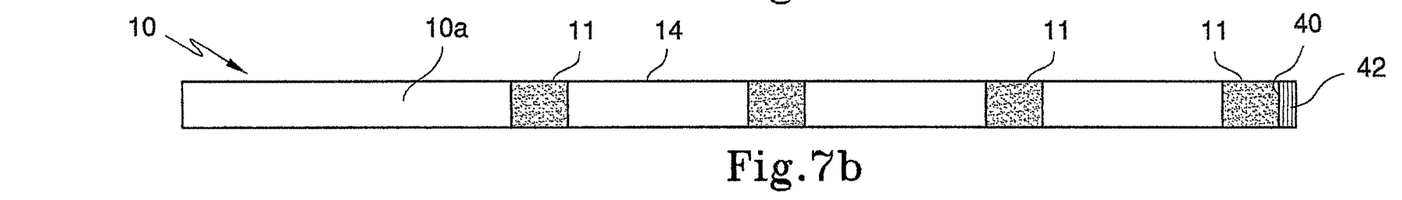
Figure 7C:
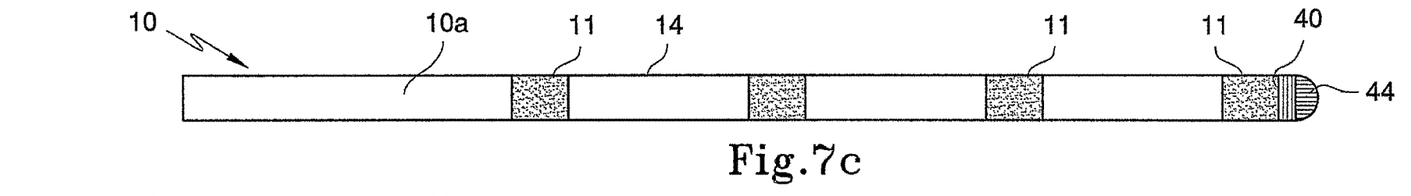

The elongate member 10a is cut at a distal end 40, as shown in FIG. 7a of the drawings, distally of one of the electrodes 11.

Figure 1:
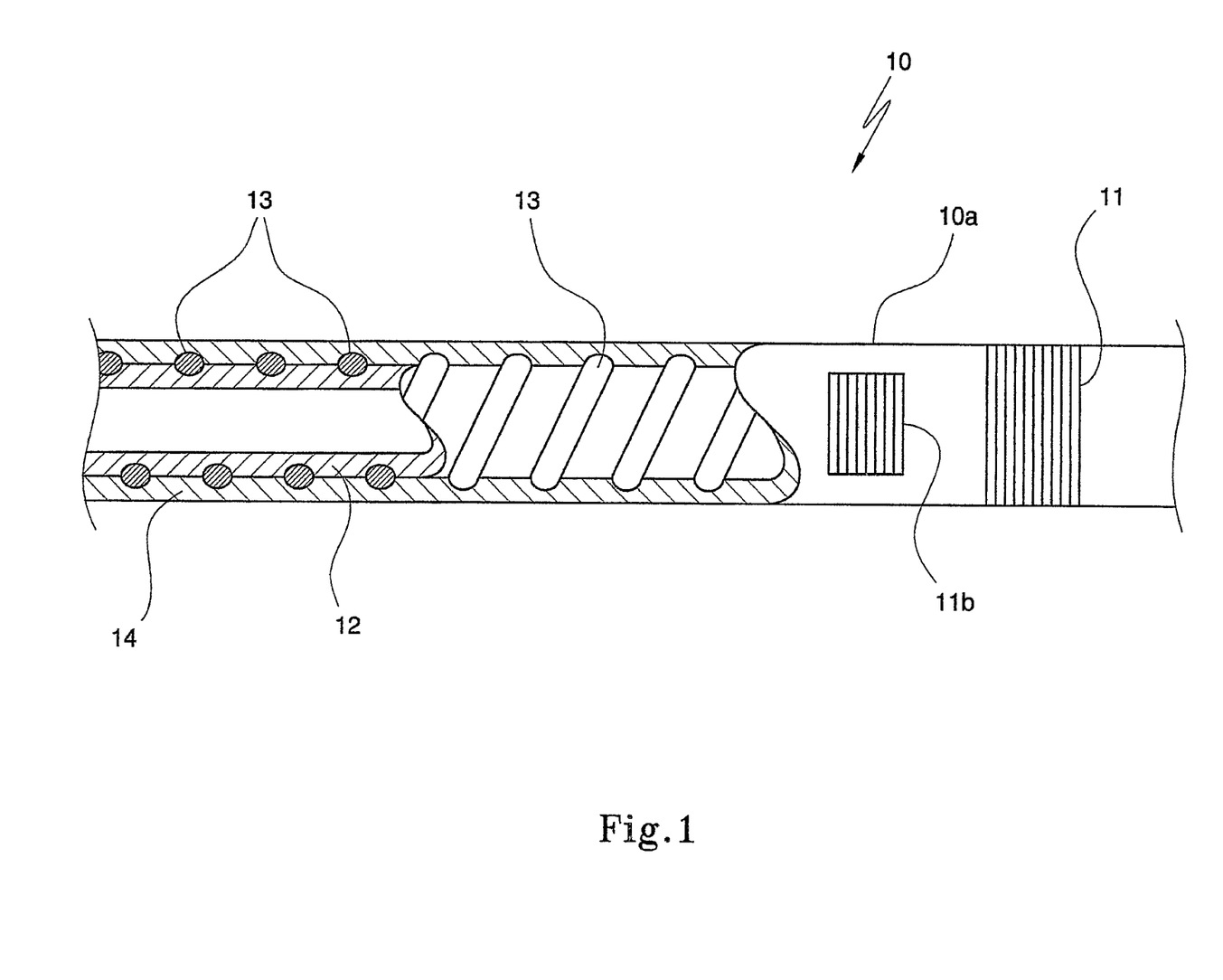
FIG. 1 is a schematic partially sectioned side view of an electrical lead in accordance with an embodiment of the invention.

A layer of an epoxy 42 is applied at the distal end 40 of the elongate member 10a to seal the distal end 40 of the elongate member 10a and to isolate the ends of the conductors 13 (FIG. 1) at the distal end 40. A further bead of epoxy 44 is applied to the layer of the epoxy 42 to form an end electrode of a required dome-shaped end 46.

Figure 7D:
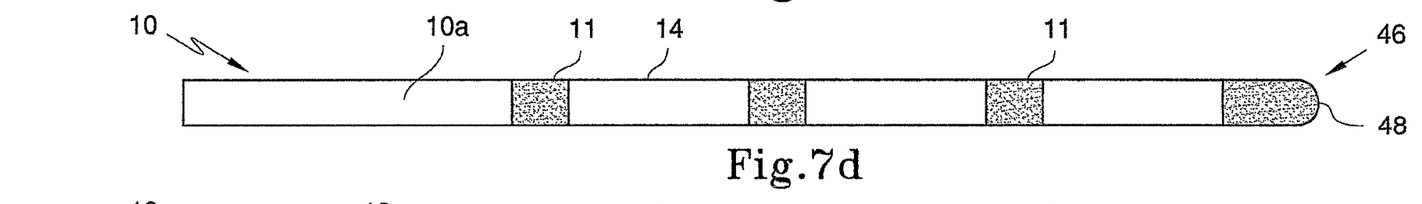

In a following step, the dome-shaped end 46 is coated with conductive silver ink of the same formulation as that used in the formation of the electrodes 11 as shown in FIG. 7d of the drawings. It will therefore be appreciated that the dome-shaped end 46 is formed prior to the application of the platinum layer 17 on the electrodes 11.

Figure 7E:
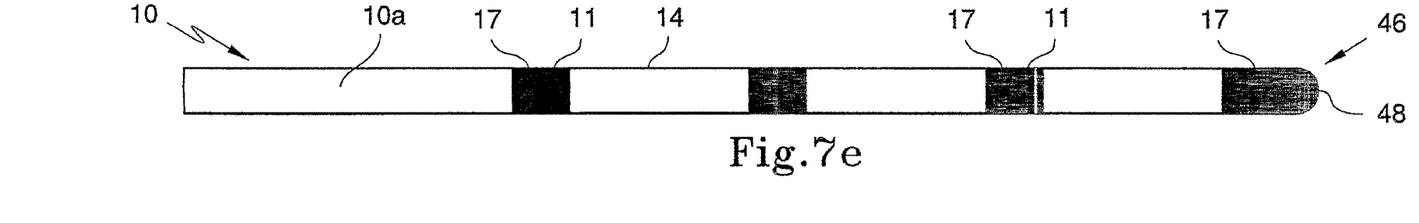

Therefore, once the dome-shaped end 46 has been coated with the silver ink, all of the electrodes 11 and an end electrode 48 are coated with a layer of platinum 17 as shown in FIG. 7e of the drawings. Once again, the platinum layer 17 is applied by electroless plating.

Referring now to FIGS. 8 through 11 of the drawings, yet a further process for manufacturing an electrical lead 10 is illustrated. Once again, with reference to the previous drawings, like reference numerals refer to like parts, unless otherwise specified.

Figure 8:
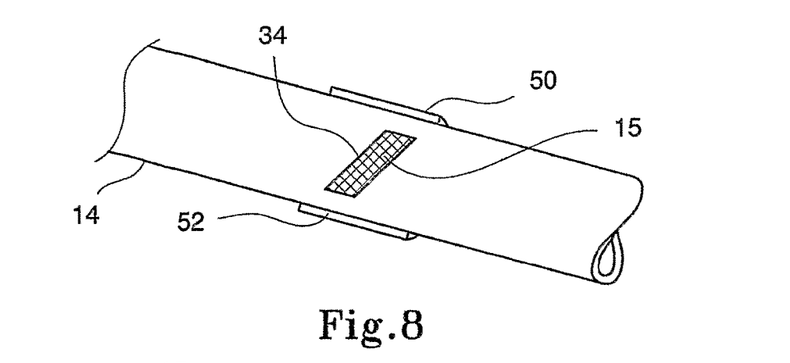
FIG. 8 shows, schematically, a perspective view of an initial step of a process, in accordance with still a further embodiment of the invention, for manufacturing an electrical lead.

In this embodiment, prior to the formation of the electrodes 11 about the outer polymeric jacket 14, once each opening 34 has been formed in the outer polymeric jacket 14, a radiopaque material 50 is applied longitudinally in register with at least some of each of the openings 34.

Figure 9:
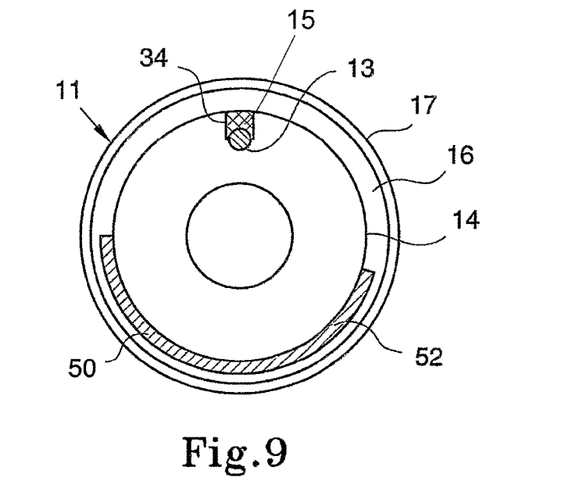
FIG. 9 is a schematic sectional end view of a first example of an electrical lead manufactured in accordance with the still further process of manufacturing an electrical lead.

In the case of the embodiment shown in FIGS. 8 and 9 of the drawings, the radiopaque material 50 is applied in the form of a cuff 52 about a part of the circumference of the outer polymeric jacket 14.

The cuff 52 is arranged on the outer polymeric jacket 14 so that it is at the same longitudinal position on the outer polymeric jacket 14 as its associated opening 34, but is arranged in diametrically opposed relationship to the opening 34 so that the radiopaque material 50 is not in electrical contact with the conductor 13 or the electrically conductive adhesive 15 in the opening 34.

The radiopaque material 50 is applied by pad printing and comprises between 70% to 80% non-conductive material and 20% to 30% adhesive. The radiopaque material 50 is a radiopaque ink sourced from Creative Materials Inc., of 141 Middlesex Road, Tyngsboro, Mass., 01879, United States of America. The adhesive part of the radiopaque material 50 is, conventionally, an epoxy. The epoxy of the radiopaque material 50 is matched to the epoxy of the silver layer 16, which is advantageous for biocompatibility purposes.

Once the radiopaque material 50 has been applied, the layer of electrically conductive silver material 16 is pad printed to overlie the radiopaque material 50 and the adhesive 15 in the opening 34. Thereafter, the platinum layer 17 is applied by electroless plating.

In the embodiment shown in FIGS. 10 and 11a through 11d of the drawings, instead of applying the radiopaque material 50 as a cuff 52, a recess 54 is formed in the outer polymeric jacket 14 in diametrically opposed relationship to the opening 34. It will be appreciated that the recess 54 is of such a depth that it does not expose any of the conductors 13 in the outer polymeric jacket 14.

Figure 10:
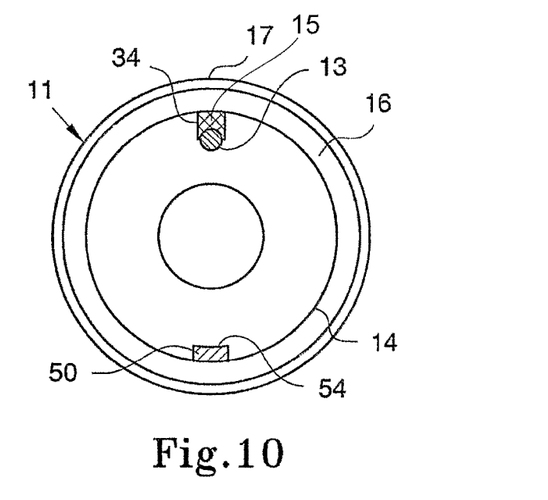
FIG. 10 is a schematic sectional end view of a second example of an electrical lead manufactured in accordance with the still further process of manufacturing an electrical lead.

The radiopaque material 50 is charged into the recess 54. In this embodiment, the epoxy of the radiopaque material 50 is selected to be the same as the epoxy used to form the electrically conductive adhesive 15 of the opening 34. Once again, this is advantageous for biocompatibility purposes.

Figure 11A:
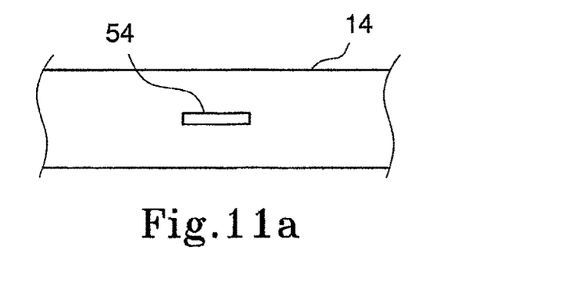
FIGS. 11a through 11d show, schematically, variations of the example of the electrical lead shown in FIG. 9.
Figure 11B:
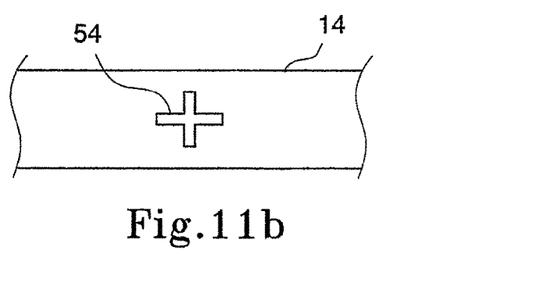
Figure 11C:
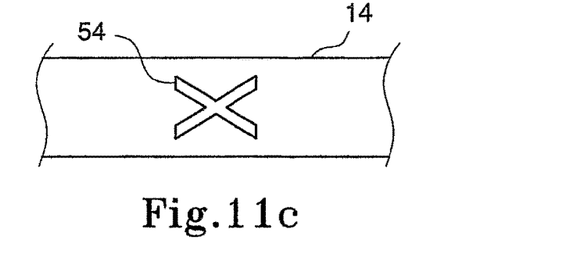
Figure 11D:
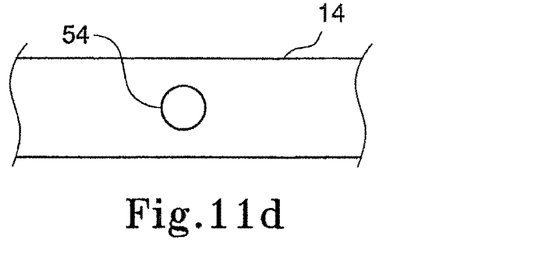

The recess 54 can be any suitable shape. Thus, as shown in FIG. 11a of the drawings, the recess 54 may be a longitudinally extending slit. Instead, as shown in FIGS. 11b and 11c of the drawings, the recess 54 could be of a cruciform shape. As shown in FIG. 11d of the drawings, the recess 54 could be a circular recess 54. It will be appreciated that any other shape of recess could equally advantageously be employed.

Once the recess 54 contains the radiopaque material 50, the silver ink 16 is applied by pad printing followed by the electroless plating of the electrode 11 with a platinum layer 17.

It will be appreciated that the silver-ink layer 16 or the platinum layer 17 need not extend over the radiopaque material 50 or the recess 54, as the case may be. It is only necessary that the radiopaque material 50 or the recess 54 be longitudinally aligned with its associated electrode 11.

It is an advantage of this embodiment that a radiopaque region is formed in alignment with the electrode 11 allowing for rapid and accurate placement of the electrode 11 by a clinician viewing the position of the electrode 11 on a fluoroscope.

It will be appreciated by persons skilled in the art that numerous variations and/or modifications may be made to this described process without departing from the spirit or scope of the broad description. The specific descriptions are, therefore, to be considered in all respects as illustrative and not restrictive.

What is claimed is:

1. A medical-use electrical lead, including:
    a tubular elongate member having a proximal end and a distal end comprising an open distalmost tip, at least one helically wound electrical conductor contained in the tubular elongate member and extending from the proximal end toward the distal end of the elongate member, the at least one helically wound electrical conductor terminating in electrical connection with a respective electrode of a plurality of electrodes each comprising a layer of electrically conductive ink on conductive adhesive materials filled in an opening of the tubular elongate member, wherein the respective electrode is located externally of the elongate member flush with the open distalmost tip; and a non-conductive termination having a first layer and a second layer, wherein the first layer of the non-conductive termination is arranged immediately adjacent to a distalmost electrode of the respective electrodes, the first layer secured to and sealing the open distalmost tip of the tubular elongate member, and wherein the second layer of the non-conductive termination is located distally on the first layer and protrudes distally of the first layer to form a desired shaped tip, a layer of conductive ink printed on the desired shaped tip and a continuous layer of electrically conductive material extending over and engaging the layer of conductive ink on the distalmost electrode and the layer of conductive ink on the desired shaped tip by electroless bonding; wherein the non-conductive termination isolates an end of the at least one helically wound electrical conductor at the distal end.

2. The lead of claim 1, wherein the non-conductive termination comprises a non-conductive resin.

3. The lead of claim 2, wherein the non-conductive termination is a synthetic resin.

4. The lead of claim 1, wherein the second layer of the non-conductive termination comprises a solid element adhesively secured to the distal end of the elongate member over the distalmost tip thereof, the solid element having the desired shape.

5. The lead of claim 1, further comprising a zone of radiopaque material on the tubular elongate member longitudinally in register with the opening and circumferentially spaced from the openeing.

6. The lead of claim 5, wherein the at least one electrically conductive material of the distalmost electrode directly overlies the zone of radiopaque material.

7. The lead of claim 5, wherein the radiopaque material comprises approximately 70% to 80% non-conductive material and about 20% to 30% of adhesive material.

8. The lead of claim 1, wherein
the opening comprises a slit arranged transversely in a wall of the tubular elongate member, the slit following a direction of the at least one helically wound electrical conductor.

9. The lead of claim 8, wherein the direction comprises a winding direction.

* * * * *

UNITED STATES PATENT AND TRADEMARK OFFICE
CERTIFICATE OF CORRECTION

PATENT NO. : 10,668,275 B2
APPLICATION NO. : 13/598506
DATED : June 2, 2020
INVENTOR(S) : Neil L. Anderson, Norman Booth and Evan K. Chong Page 1 of 1

It is certified that error appears in the above-identified patent and that said Letters Patent is hereby corrected as shown below:

In the Claims

Claim 5, Column 14, Line 9, change "from the openeing." to --from the opening.--

Signed and Sealed this
Eleventh Day of August, 2020

Andrei Iancu
*Director of the United States Patent and Trademark Office*